(12) United States Patent
Christen et al.

(10) Patent No.: US 6,500,826 B1
(45) Date of Patent: *Dec. 31, 2002

(54) USE OF PANAVERIUM BROMIDE FOR PREVENTING CELL PROLIFERATION AND DISEASES CAUSED THEREBY IN THE LIVER AND DIGESTIVE TRACT

(75) Inventors: Marie-Odile Christen, Paris Cedex (FR); Joelle Maugard, Marly le Roi (FR); Huynh Duc, Villejuif (FR); Hans Scherubl, Berlin (DE); Jan Huizinga, Ontario (CA); Michael G. Blennerhasset, Ontario (CA)

(73) Assignee: Solvay Pharma, Suresnes (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,305

(22) PCT Filed: May 6, 1997

(86) PCT No.: PCT/FR97/00809
§ 371 (c)(1),
(2), (4) Date: Apr. 26, 1999

(87) PCT Pub. No.: WO97/41859
PCT Pub. Date: Nov. 13, 1997

(30) Foreign Application Priority Data

May 6, 1996 (FR) .............................. 96/05640

(51) Int. Cl.$^7$ .......................................... A61K 31/5375
(52) U.S. Cl. .................................................. 514/239.2
(58) Field of Search ...................................... 514/239.2

(56) References Cited

FOREIGN PATENT DOCUMENTS

FR          2097032          3/1972

OTHER PUBLICATIONS

Scherubl et al., Gastroenterology, 110(4), p. A589 (abstract) Apr. 1996.*

J. Dubarry et al., "Effet a Court Term Du Bromure De Pinaverium Dans Les Oesophagites, Gastro–Duodenites et Colopathies Fonctionnelles", pp. 1457–1459, *Bordeaux Medical*, vol. 10, No. 21, 1977.

M. Newman, "Pinaverium Bromide", pp. 241–243, *Drugs Today*, vol. 13, No. 6, 1978.

M.O. Chriten, "Action of Pinaverium Bromide, a Calcium–Antagonist, on Gastrointestinal Motility Disorders", pp. 821–825, *Gen. Pharmac.*, vol. 21, No. 6, 1990.

B.A. Scheinfeld et al., "Verapamil Selectively Inhibits Inflammation–Induced Intestinal Smooth Muscle Hyperplasia in Vivo: A Potential New Therapy for Stricture Formation", one page abstract only, *Gastroenterology*, vol. 10, No. 4, 1995.

K. Sato, et al., "Inhibitory Effect of Calcium Channel Blockers on Growth of Pancreatic Cancer Cells", pp. 193–202, *Pancreas*, vol. 9, No. 2, 1994.

L. R. Zacharski et al., "Chronic Calcium Antagonist Use in Carcinoma of the Lung and Colon: A Restrospective Cohort Observational Study", pp. 451–458, *Cancer Investigation*, vol. 8, No. 5, 1990.

R. Awad et al., "Irritable Bowel Syndrome Treatment Using Pinaverium Bromide as a Calcium Channel Blocker, A Randomized Double–Blind Pacebo–Controlled Trial", pp. 137–144, *ACTA Gastroenterological Latinoamericana*, vol. 25, No. 3, 1995.

M. Halfon, "Le Traitement Des Colopathies Fonctionnelles Par Le Bromure De Pinaverium", pp. 445–446, *Medecine Interne*, vol. 15, No. 12, 1980.

* cited by examiner

*Primary Examiner*—Phyllis G. Spivack
(74) *Attorney, Agent, or Firm*—Young & Thompson

(57) ABSTRACT

The use of panaverium bromide for treating or preventing diseases of the liver and digestive tract caused by excessive cell proliferation therein, is disclosed.

14 Claims, 1 Drawing Sheet

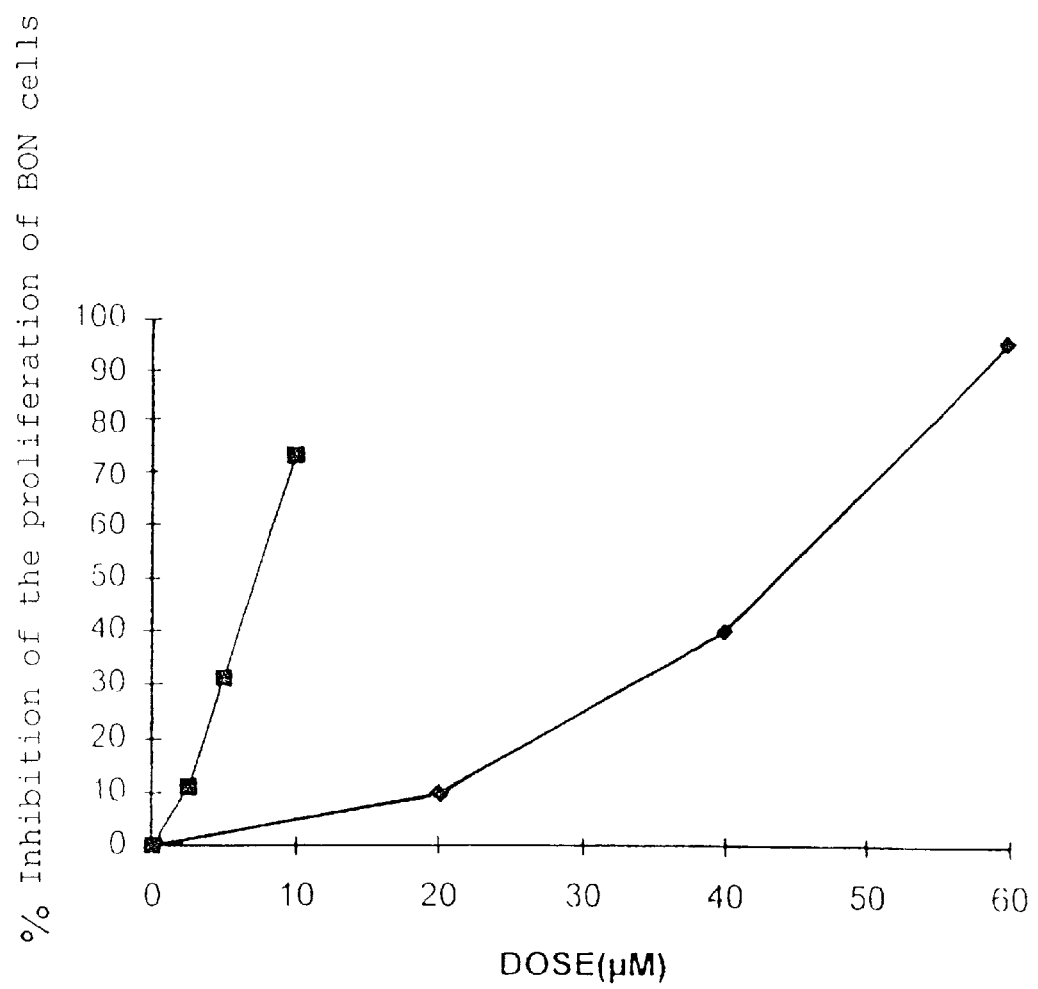

USE OF PANAVERIUM BROMIDE FOR PREVENTING CELL PROLIFERATION AND DISEASES CAUSED THEREBY IN THE LIVER AND DIGESTIVE TRACT

The present invention relates to a novel use of pinaverium bromide in gastrointestinal pathologies, inflammatory digestive diseases (IBD), colites, ulcers, Crohn's disease or functional colopathies (IBS), during which proliferative phenomena which lead to pathological complications appear.

While the constant and rapid renewal of the epithelium of the digestive tract is an important factor in the maintenance of the integrity of the mucous membrane, it is also an important factor in the development of tumours and hypertrophies.

In these latter cases, an abnormal proliferation of the epithelial cells and an increased number of proliferative zones are always observed; this is also found in patients who are at familial risk of cancer of the colon or in patients who are suffering from diseases which predispose to cancer of the digestive tract (chronic gastrites, inflammatory digestive diseases, Crohn's disease, ulcerative colites, colonic polyps, etc.). Furthermore, it has been shown that inflammation of the intestine can give rise to hypertrophy and hyperplasia of the smooth muscle cells at one and the same time. This results in a thickening of the muscle wall, and therefore in a change in its motility, resulting in the appearance of complications which require surgical treatments.

In addition, inhibition of the proliferation of neoplastic cells is a determining factor in the prevention and treatment of cancers and metastases of the digestive tract.

Pinaverium bromide is the only calcium antagonist which is selective for the intestinal tract and which has spasmolytic activity and which is prescribed for the chronic treatment of functional digestive disorders (irritable bowel syndrome or IBS). This compound has been described, in particular, in French patent 2 097 032.

The authors of the present invention have now surprisingly demonstrated, by means of studies carried out in vitro, that pinaverium bromide is able to inhibit the proliferation of neoplastic and hyperplastic cells of the digestive tract, with this inhibition being greater than that brought about by another calcium antagonist, i.e. verapamil. Furthermore, a study carried out in vivo also demonstrated the efficacy of pinaverium bromide in decreasing tumours induced in animals.

Pinaverium bromide can therefore be used as a medicament for preventing cancer of the digestive tract both in the healthy individual and the individual suffering from a digestive pathology such as IBS. In the latter individual, it will then exert a prophylactic or therapeutic effect which complements its effect on the IBS.

This compound may also be used for the therapeutic treatment of hepatocarcinoma or of cancer of the pancreas and, more generally, of any cancer of the hepatodigestive tract.

The present invention therefore relates to the use of pinaverium bromide for preparing a medicament which is intended for preventing or treating diseases of the hepatodigestive tract which are due to excessive proliferation of the cells of the tract.

More especially, the invention relates to the use of pinaverium bromide for preparing a medicament which is intended for preventing or treating intestinal cellular hyperplasias which are linked to inflammatory digestive diseases, or for preventing hypertrophies of the smooth-muscle-cell wall of the intestinal tract and motor disturbances which are due to the inflammatory diseases of the digestive tract (inflammatory bowel disease or IBD, Crohn's disease or ulcerative colitis) which are characteristic of the IBS.

The invention is also directed towards using pinaverium bromide for preparing a medicament which is intended for preventing or treating a cancer of the hepatodigestive tract, comprising cancer of the colon and of the stomach, hepatocarcinoma and cancer of the pancreas, or else the carcinoid syndrome or functional diseases which are linked to the carcinoid tumours.

It also relates to the use of pinaverium bromide for preparing a medicament which is intended for preventing and treating cancer of the hepatodigestive tract in patients who are suffering from irritable syndromes of the colon (irritable bowel syndrome or IBS), while effecting a complementary and simultaneous treatment of the symptoms which are characteristic of the TBS.

The invention also comprises a method for the prophylactic or therapeutic treatment of diseases of the hepatodigestive tract which are due to excessive proliferation of the cells of the tract, which method consists in administering a medicament containing pinaverium bromide, as the active principle, to a patient.

Finally, the method is directed towards using pinaverium bromide for producing a medicament which is intended for treating inflammatory digestive diseases such as IBD (inflammatory intestinal disease or inflammatory bowel disease), Crohn's disease or ulcerative colitis, which diseases are generally associated with the thickening of the mucous membrane.

Preferably, within the context of the present invention, the pinaverium bromide is used by being administered in a daily quantity of between 50 mg and 450 mg. Administration is by the oral route or by the injectable route, using a solution which is dosed at from 0.2 to 1 mg/ml.

The advantages of the invention emerge in more detail in the tests which are described below.

In addition, the following figure shows the effect of pinaverium bromide (—■—) on inhibition of the growth of pancreatic carcinoid cells as compared with the effect of verapamil (—◊—).

Test 1:

Inhibition of the proliferation of colon cancer cells by pinaverium bromide as compared with the inhibition induced by another calcium inhibitor (verapamil)

The HT29 colon cancer cell line employed (originally isolated from an adenocarcinoma of the human colon) was obtained from the ATCC (American Type Culture Collection).

The cells are cultured at the rate of $10^4$ or $5 \times 10^4$ cells in a well containing 200 $\mu$l of culture medium composed of RPMI 1460 supplemented with 10% fetal calf serum, 2 mM of L-glutamine and 25 $\mu$M gentamicin. Pinaverium bromide (or verapamil), dissolved in 50% ethanol or DMSO, is added to the cell culture at various concentrations, and the percentage inhibition of cell proliferation is assessed by measuring the incorporation of tritiated thymidine ($^3$HThdR), with the latter being added to each well at the rate of 37 KBq (1 $\mu$Ci); the contents of the wells are withdrawn and counted 15 hours later using a "Filter Mate™ Cell Harvester and Matrix 9600™ Direct Beta Counter" (Packard).

The results are as follows:

| | Concentration of the product tested (% by weight) | % Inhibition pinaverium bromide | % Inhibition verapamil |
|---|---|---|---|
| $^3$HThdR | 0.025 | 78 | 17 |
| | 0.05 | 82 | 17 |
| | 0.1 | 86 | 27 |

The inhibitory effect of the pinaverium bromide is from 3 to 5 times greater than that of the verapamil.

Test 2:

Effect of pinaverium bromide on hepatocarcinoma cells.

LFC rat hepatocarcinoma cells (VPR42, Villejuif) are cultured at the rate of $10^4$ or $5 \times 10^4$ cells in a well containing 200 µl of culture medium. The products to be tested (pinaverium bromide and verapamil) are dissolved in 50% ethanol and used at concentrations of 0.1% and 1% by weight.

Inhibition of cell proliferation is assessed using tritiated thymidine as described in Test 1. The assessment is made in comparison with the reference product, which is verapamil. The results show a percentage inhibition of proliferation of from 85 to 88% in the case of pinaverium bromide and of 72% in the case of verapamil.

Test 3:

Effect of pinaverium bromide on the growth of STC-1 carcinoid intestinal cells

The STC-1 mouse intestinal cancer cell lines are cultured in a DMEM medium which contains 15% horse serum and 2.5% FCS. The products to be studied are added to the culture and cell growth is assessed by counting cells or, more frequently, by a fluorescence technique which is based on the cellular enzymic hydrolysis of the fluorogenic substrate 4-methylumbelliferyl heptanoate (MUH) ; thus, viable cells which are incubated with MUH generate a fluorescent signal which is proportional to their number and which is determined using a "Titentec Fluoroscan II" (Flow Laboratory), with the value being given in arbitrary fluorescence units.

Pinaverium bromide was found to be twice as active as verapamil in the test.

($ED_{50}$ PINAVERIUM=7 µM; $ED_{50}$ VERAPAMIL=13 µM)

Test 4:

Study of the inhibition by pinaverium bromide of the growth of BON pancreatic carcinoid cells The BON human pancreatic carcinoid cell lines are cultured in a DMEM/F12K (1/1) medium to which 10% FCS is added. The verapamil and the pinaverium bromide are added to the culture and cell growth is determined after 8 days by means of a fluorescence technique such as that described in Test 3.

The results reported in the figure demonstrate the efficacy of pinaverium bromide in inhibiting the growth of the BON pancreatic carcinoid cells, and its superiority to verapamil ($ED_{50}$ PINAVERIUM=7.2 µM; $ED_{50}$ VERAPAMIL=43.6 µM).

Test 5:

Inhibition by pinaverium bromide of the hyperplasia of rat intestinal smooth muscle cells which is induced by PDGF (platelet-derived growth factor)

The intestinal smooth muscle cells are cultured in a culture medium containing 10% fetal bovine serum and then exposed to PDGF (growth factor found during inflammations) for 20 hours. Cell growth is assessed by the incorporation of tritiated thymidine.

Pinaverium bromide ($10^{-5}$ M) totally inhibits the growth of the intestinal smooth muscle cells which is induced by the inflammation factor PDGF. It therefore has a beneficial effect on inflammation phenomena of the digestive tract.

Test 6:

Effect of pinaverium bromide on the diameters of the tumours which are induced in nude mice.

The tumours are induced by subcutaneously injecting HT29 colon cancer cells into nude mice.

Pinaverium bromide is injected intraperitoneally a few hours before injecting the HT29 cells.

Tumour development is assessed by measuring the diameter of the induced local tumour in relation to the duration of the experiment, which is 44 days.

A 30% reduction in the diameter of the tumours is observed from the 25th day of the experiment onwards.

What is claimed is:

1. A method for inhibiting hyperproliferation of hepatodigestive tract cells connected with diseases of the hepatodigestive tract which affect the stomach, the intestines, the colon and the liver, comprising administering to a person suffering from or subject to a disease associated with said hyperproliferation a pharmaceutically effective amount of pinaverium bromide, said amount being effective to inhibit said hyperproliferation.

2. The method according to claim 1, wherein said diseases of the hepatodigestive tract are diseases associated with intestinal cellular hyperplasia, hypertrophy of the smooth-muscle-cell wall of the intestinal tract or motility disturbances.

3. The method according to claim 1, wherein said inhibition of hyperproliferation of hepatodigestive tract cells inhibits cancer of the hepatodigestive tract.

4. The method according to claim 1, wherein said amount is from 50 to 450 mg per day.

5. The method according to claim 4, wherein said amount is administered in a solution dosed at from 0.2 to 1 mg/ml.

6. The method according to claim 5, wherein said amount is administered orally or by injection.

7. A method for inhibiting hyperproliferation of hepatodigestive tract cells comprising administering to a person suffering from or subject to a disease associated with the hyperproliferation of hepatodigestive tract cells a pharmaceutically effective amount of pinaverium bromide, said amount being effective to inhibit said hyperproliferation, wherein said diseases of the hepatodigestive tract are selected from the group consisting of colon cancer, stomach cancer and hepatocarcinoma.

8. The method according to claim 7, wherein said amount is administered in a solution dosed at from 0.2 to 1 mg/ml.

9. The method according to claim 7, wherein said amount is from 50 to 450 mg per day.

10. The method according to claim 7, wherein said amount is administered orally or by injection.

11. The method according to claim 7, wherein said amount is administered in a solution dosed at from 0.2 to 1 mg/ml.

12. The method according to claim 7, wherein said amount is administered orally or by injection.

13. A method for inhibiting hyperproliferation of hepatodigestive tract cells comprising administering to a person suffering from or subject to a disease associated with the hyperproliferation of hepatodigestive tract cells and thickening of mucous membrane, a pharmaceutically effective amount of pinaverium bromide, said amount being effective to inhibit said hyperproliferation, and wherein said diseases of the hepatodigestive tract are selected from the group consisting of inflammatory intestinal disease, Crohn's disease and ulcerative colitis.

14. The method according to claim 13, wherein said amount is from 50 to 450 mg per day.

* * * * *